(12) United States Patent
Butts et al.

(10) Patent No.: US 7,118,733 B2
(45) Date of Patent: *Oct. 10, 2006

(54) TOPICAL SILICONE COMPOSITIONS AND METHOD FOR MAKING

(75) Inventors: Matthew David Butts, Rexford, NY (US); Christopher Michael Byrne, Ithaca, NY (US); Steven James Stoessel, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 296 days.

This patent is subject to a terminal disclaimer.

(21) Appl. No.: 09/951,004

(22) Filed: Sep. 14, 2001

(65) Prior Publication Data

US 2003/0082127 A1    May 1, 2003

Related U.S. Application Data

(63) Continuation-in-part of application No. 09/616,534, filed on Jul. 14, 2000, now Pat. No. 6,390,102, and a continuation-in-part of application No. 09/616,535, filed on Jul. 14, 2000, now Pat. No. 6,619,294.

(51) Int. Cl.
*A61Q 5/12* (2006.01)
*A61K 8/00* (2006.01)

(52) U.S. Cl. .................. 424/70.1; 424/70.12
(58) Field of Classification Search ............ 424/70.1, 424/70.12; 514/63; 132/202
See application file for complete search history.

(56) References Cited

U.S. PATENT DOCUMENTS

| | | |
|---|---|---|
| 4,567,039 A | 1/1986 | Stadnick et al. |
| 4,859,460 A | 8/1989 | Mahieu et al. |
| 4,973,475 A | 11/1990 | Schnetzinger et al. |
| 5,030,756 A | 7/1991 | Deppert et al. |
| 5,087,733 A | 2/1992 | Deppert et al. |
| 5,160,733 A | 11/1992 | Berthiaume |
| 5,206,013 A | 4/1993 | Deppert et al. |
| 5,211,942 A | 5/1993 | Deppert et al. |
| 5,254,335 A | 10/1993 | Deppert et al. |
| 5,350,572 A | 9/1994 | Savaides et al. |
| 5,523,080 A | 6/1996 | Gough et al. |
| 5,525,332 A | 6/1996 | Gough et al. |
| 5,609,856 A | 3/1997 | Dubief et al. |
| 5,609,861 A | 3/1997 | Dubief et al. |
| 5,969,077 A | 10/1999 | Schrock et al. |
| 6,390,102 B1 * | 5/2002 | Butts et al. ............ 132/202 |
| 6,488,921 B1 * | 12/2002 | Butts et al. ............ 424/70.1 |
| 6,506,371 B1 * | 1/2003 | Butts et al. ............ 424/70.1 |
| 6,544,499 B1 * | 4/2003 | Glenn et al. ............ 424/70.1 |
| 6,619,294 B1 * | 9/2003 | Butts et al. ............ 132/202 |

FOREIGN PATENT DOCUMENTS

| | | |
|---|---|---|
| EP | 0159628 | 4/1985 |
| EP | 0509922 | 4/1992 |
| WO | 9935180 | 12/1997 |
| WO | 9838974 | 4/1998 |
| WO | 0040210 | 1/2000 |

OTHER PUBLICATIONS

"Development of Novel Attachable Initiator for "Living" Radical Polymerization and Synthesis of Polysiloxane Block Copolymer", Nakagawa and Matyjaszewski, Amer. Chem. Soc., Polym. Preprints 1996, 270-271.
Chemical Abstracts, Columbus, Ohio XP-002153987 "Effect of Ultrasonic Vibrations During Crystallization on the Properties of Nickel-aluminum Alloy Catalysts Containing Zirconium and Molybdenum Additives", Omarov et al.
Chemical Abstracts, Columbus, Ohio XP-002153988 "Study of the Phase Composition and Structure of Cobalt-70% Aluminum Alloy Catalysts Containing Copper, Manganese and Iron", Omarov et al., vol. 87, No. 8, 1977.

* cited by examiner

*Primary Examiner*—Woodword Michael
*Assistant Examiner*—Desta Yebassa
(74) *Attorney, Agent, or Firm*—Shawn A. McClintic; William E. Powell, III

(57) ABSTRACT

A silicone composition is provided which comprises at least one polysiloxane or silicone resin, and at least one molecular hook wherein the molecular hook comprises a hexafluorophosphate counterion, a tetrafluoroborate counterion, a triflate counterion, or combinations thereof. Further embodiments of the present invention include a method for substantially increasing the thermal stability of a silicone composition and a method for making the silicone composition.

48 Claims, No Drawings

TOPICAL SILICONE COMPOSITIONS AND METHOD FOR MAKING

This application is a continuation in part of applications Ser. No. 09/616,534 (now U.S. Pat. No. 6,390,102) and Ser. No. 09/616,535 (now U.S. Pat. No. 6,619,294) filed Jul. 14, 2000.

BACKGROUND OF THE INVENTION

The present invention relates to compositions for personal care products. More particularly, the present invention relates to silicone compositions which achieve conditioning benefits in hair care products.

Silicones are widely used in hair care products due in part to the conditioning benefits that they impart to hair. In most applications, the silicone is deposited on hair out of a matrix but is often held only by weak physical forces, such as hydrogen bonding or van der Waals interactions. Because the interactive forces are weak, the benefits of silicone by deposition are generally short lived. Another issue with silicone conditioning agents is that conditioning benefits are often attributed to the deposition of high molecular weight, high viscosity fluids and gums that can weigh down the hair. Beneficial conditioning effects can also be caused by treating hair with silanol capped amino-functionalized silicones. These silicones can undergo condensation cure reactions on hair to form somewhat durable films.

It is widely known by those skilled in the art that covalent bonding is one key to "permanent" hair treatment. Processes which alter the structure of the hair, such as permanent wave and color treatment methods, do provide longer lasting effects. These processes include glycolate reduction and peroxide reoxidation. A significant disadvantage of these processes is that they are very damaging to hair and can only be carried out infrequently.

Gough et al. in U.S. Pat. Nos. 5,523,080 and 5,525,332 describe the synthesis of silicone-azlactone polymers which exhibit covalent bonding and "permanent" conditioning benefit. Gough et al. discuss incorporating an azlactone-functionalized copolymer which consists of vinylazlactone and methacryloyl polydimethylsiloxane monomers into a silicone-active group-hair structure. The hair treatment using the silicone-azlactone polymers does not consist of the steps of reduction with a glycolate or reoxidation with peroxide.

It is desirable to produce silicone compositions which can be used to treat damaged hair and provide durable benefits. Thus, silicone products are constantly being sought which can both covalently bond to hair as well as impart hair care benefits appreciated by consumers.

BRIEF SUMMARY OF THE INVENTION

The present invention provides a silicone composition which comprises at least one polysiloxane or silicone resin, at least one linker, and at least one molecular hook wherein the molecular hook comprises a hexafluorophosphate countering a tetrafluoroborate counterion, a triflate counterion, or combinations thereof.

The present invention further provides a method for making a silicone composition comprising
(1) reacting at least one polysiloxane or silicone resin with at least one linker to form a linker-substituted polymer; and
(2) reacting the linker-substituted polymer with at least one molecular hook to form a hook-linker-polymer product wherein the molecular hook moiety in the product comprises a hexafluorophosphate counterion, a tetrafluoroborate counterion, a triflate counterion, or combinations thereof.

The present invention further provides a method for substantially increasing the thermal stability of a silicone composition comprising providing at least one molecular hook with a hexafluorophosphate counterion, a tetrafluoroborate counterion, a triflate counterion, or combinations thereof; a linker; and a polysiloxane or silicone resin wherein the silicone composition has a percent decomposition of less than about 30% for a time period of 4 weeks at a temperature of about 40° C. in acetone.

DETAILED DESCRIPTION OF THE INVENTION

The present invention includes a silicone composition which includes at least one polysiloxane or silicone resin, at least one linker, and at least one molecular hook. The molecular hook includes at least one counterion wherein the counterion is hexafluorophosphate, tetrafluoroborate, triflate, or combinations thereof, and the silicone compositions are significantly more stable than when the silicone compositions includes typical halide ions. "Significantly more stable" as used herein refers to a measurably greater time of thermal stability in solvent, as determined by nuclear magnetic resonance spectroscopy, when the silicone composition comprises hexafluorophosphate, tetrafluoroborate and triflate counterions versus halide counterions. Typically, the silicone composition has, for example, a percent decomposition of less than about 30% for a time period of 4 weeks at a temperature of about 40° C. in acetone.

The linker is bound to both a molecular hook and to an atom of a polysiloxane or silicone resin. Preferably the linker is bound to a polysiloxane or silicone resin through a silicon (Si), carbon (C), oxygen (O), nitrogen (N), or sulfur (S) atom, and most preferably through a silicon atom. When more than one linker is present, it is also contemplated that linkers may be bound to a polysiloxane or silicone resin through more than one type of atom, for example through both silicon and carbon atoms.

The molecular hook may be selected from the range consisting of heterocyclic molecular hooks, $sp^2$ aliphatic trigonal carbon molecular hooks, $sp^3$ carbon molecular hooks, metal based molecular hooks, non-metal and metalloid based molecular hooks, energy-sensitive molecular hooks and mixtures thereof. The molecular hook is preferably selected from the range consisting of heterocyclic molecular hooks, $sp^2$ aliphatic trigonal carbon molecular hooks, $sp^3$ carbon molecular hooks and non-metal molecular hooks. The molecular hook is more preferably selected from heterocyclic molecular hooks, $sp^2$ aliphatic trigonal carbon molecular hooks and non-metal molecular hooks.

The molecular hook of the present invention preferably comprises a sulfur-containing compound wherein the sulfur-containing protective group may be a heterocyclic ring or ring system. Heterocyclic groups that are suitable for use in the present invention include mono- or polyunsaturated or saturated heterocyclic rings, heterocyclic ring systems, fused heterocyclic ring systems, substituted heterocyclic rings, substituted heterocyclic ring systems or substituted fused heterocyclic ring systems. The heterocyclic rings contain in a range between about three and about thirty atoms, and may contain electronegative heteroatoms including N, O, S, or P. The heterocyclic rings or ring systems also may contain exocyclic double bonds of the C=M type wherein M is O, S, $NE^1$ or $CE^1E^2$. $E^1$ and $E^2$ used here, and E, $E^3$, and $E^4$ used hereinafter, each represent, independently from one another, a monovalent group which can be a silicone group, H or any of the following: a straight, branched or mono- or polycyclic aliphatic, mono or polyunsaturated alkyl, aryl, heteroalkyl, heteroaliphatic or heteroolefinic system including carbon atoms in a range between about 1 and about 30 together with heteroatoms in a range between about 0 and about 15, especially O, N, S, P, Si, and can incorporate one or more substituents including, but not limited to, mono, poly or perfluoro substitution.

In particular, the molecular hook may be a heterocyclic pyridinium compound (I), a heterocyclic triazinium compound (II), a heterocyclic pyrimidinium compound (III), or a heterocyclic pyrazine compound (IV):

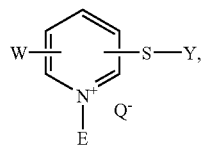

(I)

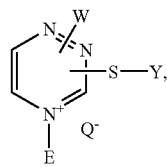

(II)

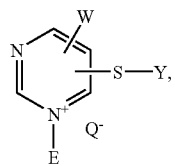

(III)

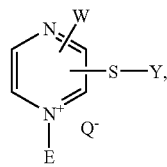

(IV)

wherein W represents optional substituents on the heterocyclic ring or ring system, Y represents the linker, $Q^-$ represents the counterion, and E is defined above. The preferred molecular hook is the pyrimidinium molecular hook of formula (III).

Optional substituents, W, which can be present on the heterocyclic ring or ring system can be selected from electron withdrawing, electron neutral, or electron donating groups with Hammett sigma para values between −1.0 and +1.5 comprising carbon-linked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1(NE^2)$, $SONE^1E^2$; O-linked groups including $OE^1$, OCN, $ONE^1E^2$; N-linked groups including $NE^1E^2$, $NE^1E^2E^{3+}$, $NE^1OE^2$, $NE^1SE^2$, NCO, NCS, $NO_2$, $N=NE^1$, $N=NOE^1$, $NE^1CN$, $N=C=NE^1$, $NE^1NE^2E^3$, $NE^1NE^2NE^3E^4$, $NE^1N=NE^2$; other miscellaneous groups including $CONE^1_2$, $CONE^1COE^2$, $C(=NE^1)NE^1E^2$, CHO, CHS, CN, NC, Hal, and derived groups that connect one or more of the optional substituents via a ring system; Hal is fluorine, chlorine, bromine, or iodine. E, $E^1$, $E^2$, $E^3$, and $E^4$ are defined above. The substituent E is preferably methyl.

Additional hook structures include compound of the formulas (V) or (VI):

(V)

(VI)

wherein R is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;

$Q^-$ is the counterion;

L is the linker;

j is in a range between about 1 and about 15.

The present invention includes a silicone composition having the formula:

$$M_a M'_b D_c D'_d T_e T'_f Q_g$$

where the subscripts a, b, c, d, e, f and g are zero or a positive integer, subject to the limitation that the sum of the subscripts b, d and f is at least one; where M has the formula:

$R^{37}_3 SiO_{1/2}$,

M' has the formula:

$(Z-Y)_h R^{38}_{3-h} SiO_{1/2}$,

D has the formula:

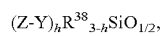

$R^{39}_2 SiO_{2/2}$,

D' has the formula:

$(Z-Y)_{(2-i)} R_i^{40} SiO_{2/2}$,

T has the formula:

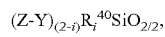

$R^{41} SiO_{3/2}$,

T' has the formula:

$(Z-Y)SiO_{3/2}$,

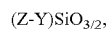

and Q has the formula $SiO_{4/2}$, where subscript h is in a range between 1 and 3; subscript i is 0 or 1; each $R^{37}$, $R^{38}$, $R^{39}$, $R^{40}$, $R^{41}$ is independently at each occurrence a hydrogen atom, $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl which groups may be halogenated, for example, fluorinated to contain fluorocarbons such as $C_{1-22}$ fluoroalkyl, or may contain amino groups to form aminoalkyls, for example aminopropyl or aminoethylaminopropyl, or may contain polyether units of the formula $(CH_2CHR^{42}O)_k$ where $R^{42}$ is $CH_3$ or H and "k" is in a range between about 4 and about 20; Z, independently at each occurrence, represents a molecular hook; and Y, independently at each occurrence, represents a linker. The term "alkyl" as used in various embodiments of the present invention is intended to designate both normal alkyl, branched alkyl, aralkyl, and cycloalkyl radicals. Normal and branched alkyl radicals are preferably those containing carbon atoms in a range between about 1 and about 30, and include as illustrative non-limiting examples methyl, ethyl, propyl, isopropyl, butyl, tertiary-butyl, pentyl, neopentyl, hexyl, and dodecyl. Cycloalkyl radicals represented are preferably those containing ring carbon atoms in a range between about 4 and about 12. Some illustrative non-limiting examples of these cycloalkyl radicals include cyclobutyl, cyclopentyl, cyclohexyl, methylcyclohexyl, and cycloheptyl. Preferred aralkyl radicals are those containing carbon atoms in a range between about 7 and about 14; these include, but are not limited to, benzyl, phenylbutyl, phenylpropyl, and phenylethyl. Aryl radicals used in the various embodiments of the present invention are preferably those containing ring carbon atoms in a range between about 6 and about 14. Some illustrative non-limiting examples of these aryl radicals include phenyl, biphenyl, and naphthyl. An illustrative non-limiting example of a halogenated moiety suitable is trifluoropropyl.

The polysiloxanes or silicone resins of the present invention are typically prepared by the hydrosilylation of an organohydrogen silicone having the formula:

$$M_a M^H_b D_c D^H_d T_e T^H_f Q_g$$

where the subscripts a, b, c, d, e, f and g are zero or a positive integer, subject to the limitation that the sum of the subscripts b, d and f is one or greater; M, D, T and Q are defined as above;

$M^H$ has the formula:

$$R^{38}_{3-h} H_h SiO_{1/2},$$

$D^H$ has the formula:

$$H_{2-i} R^{40}_i SiO_{2/2},$$

$T^H$ has the formula:

$$HSiO_{3/2},$$

where each $R^{38}$ and $R^{40}$ is independently as defined above; and subscript h and subscript i are defined above.

Hydrosilylation is typically accomplished in the presence of a suitable hydrosilylation catalyst. The catalysts preferred for use with these compositions are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in *Advances in Organometallic Chemistry*, volume 17, pages 407 through 447, F. G. A. Stone and R. West editors, published by the Academic Press (New York, 1979). A preferred catalyst contains platinum. Persons skilled in the art can easily determine an effective amount of platinum catalyst. Generally, an effective amount is in a range between about 0.1 parts per million and about 100 parts per million of the total silicone composition.

The organohydrogen silicone compounds that are the precursors to the compounds of the present invention may be prepared by the process disclosed in U.S. Pat. No. 5,420,221. The '221 patent discloses the redistribution of polydimethylsiloxane polymers with organohydrogen silicone polymers and optionally, added chain stopper, to provide a silicone with randomly-distributed hydride groups using a Lewis acid catalyst, preferably a phosphonitrilic compound. Hydride-terminated polymers can be made in related equilibration reactions.

Synthesis of the polysiloxane or silicone resin may also be performed by other methods known to those skilled in the art, for example, the hydrosilylation of a monomer such as methyldichlorosilane could be followed by co-hydrolysis with the appropriate dialkyldichlorosilane and optionally, chlorotrimethylsilane.

It is to be noted that as pure compounds, the subscripts describing the organohydrogen siloxane precursor and the hydrosilylation adduct of the present invention are integers as required by the rules of chemical stoichiometry. The subscripts will assume non-integral values for mixtures of compounds that are described by these formulas. The restrictions on the subscripts heretofore described for the stoichiometric subscripts of these compounds are for the pure compounds, not the mixtures.

In specific embodiments of the present invention, the silicone composition typically comprises at least one compound of the following formulas, (VII), (VIII), (IX), (X), (XI), or (XII):

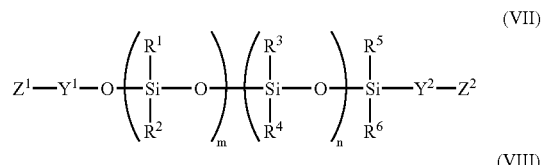

(VII)

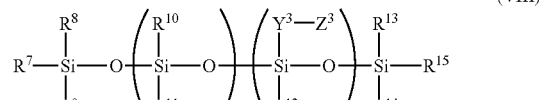

(VIII)

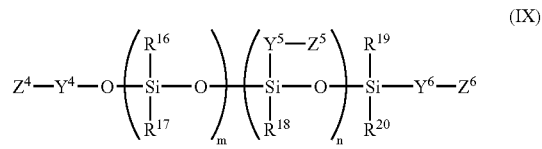

(IX)

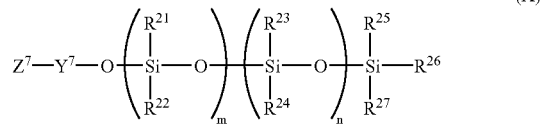

(X)

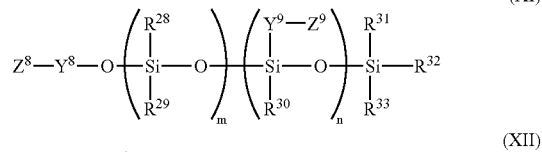

(XI)

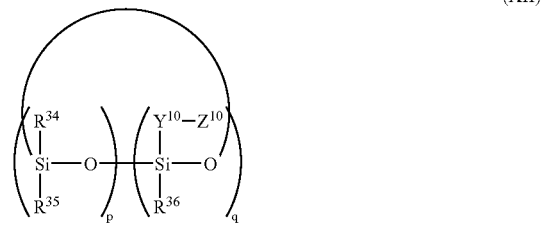

(XII)

where each $R^1$–$R^{36}$ is independently at each occurrence a hydrogen atom, $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl which groups may be halogenated, for example, fluorinated to contain fluorocarbons, may contain amino groups to form aminoalkyls, or may contain polyether units; $Z^{1-10}$, independently at each occurrence, represents a molecular hook; and $Y^{1-10}$, independently at each occurrence, represents a linker; wherein "m" in each formula has a value in a range between about 0 and about 13,000, preferably about 0 and about 1000, more preferably between about 1 and about 250, still more preferably between about 5 and about 250, even more preferably between about 10 and about 150, and most preferably between about 20 and about 120; "n" in each formula has a value in a range between about 0 and about 13,000, more preferably between about 0 and about 50, more preferably between about 1 and about 20, still more preferably between about 2 and about 10, and most preferably between about 2 and about 5 with the proviso that in formula (VIII) "n" is not 0; "m+n" in each formula has a value in a range between about 1 and about 26,000, preferably in a range between about 3 and about 250, and more preferably between about 5 to about 150; "q" has a value of at least one and "p+q" has a value of at least 3, preferably in a range between about 3 and about 20, more preferably in a range between about 3 and about 10, and most preferably in a range between about 3 and 6. $R^{1-36}$ is preferably methyl. The preferred silicone composition includes a compound of the formula (VII) or (VIII). When the silicone composition is of formula (XII), "a", "b", and "g" have a value of at least one. The polysiloxane or silicone resin typically has a molecular weight in a range between about 100 and about 6,000,000, preferably in a range between about 250 and about 50,000, more preferably in a range between about 500 and about 25,000, and most preferably in a range between about 500 and about 15,000.

In one embodiment of the present invention, a polysiloxane- or silicone resin-containing composition includes a preponderance of a specific linear, branched, cross-linked, or cyclic polysiloxane or silicone resin. In other embodiments of the present invention, a polysiloxane- or silicone resin-containing composition comprises a mixture of polysiloxanes, mixture of silicone resins, or mixtures of polysiloxanes and silicone resins which may include linear, branched, cross-linked, and cyclic species. Also, suitable compositions may comprise one or more polysiloxanes, silicone resins, and mixtures thereof which may contain adventitious amounts of other species at a level in a range between about 0.0001 wt. % and about 5 wt. % based on total silicon-containing species, for example, arising during the synthesis process for said polysiloxanes or silicone resins. In illustrative examples, suitable compositions may contain adventitious amounts of $D_4$, or species containing Si—H, Si—OH, Si—O-alkyl bonds, and mixtures thereof.

The linker comprises any $C_1$–$C_{250}$ alkyl, aryl, or alkylaryl group where the $C_{1-250}$ group can be interrupted by or substituted with aromatic groups or aromatic-containing groups. The $C_{1-250}$ group may also contain one or more heteroatoms such as O, N, or S. Furthermore, the $C_{1-250}$ group may be unsubstituted or substituted with heteroatoms such as halogen. Typically, the linker has the formulas (XIV) through (XX)

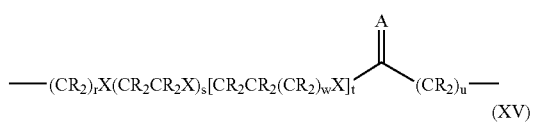

(XIV)

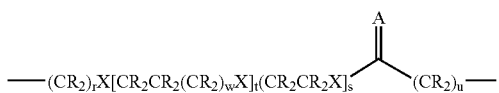

(XV)

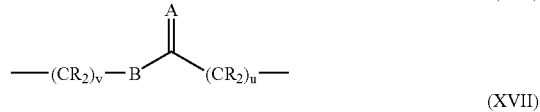

(XVI)

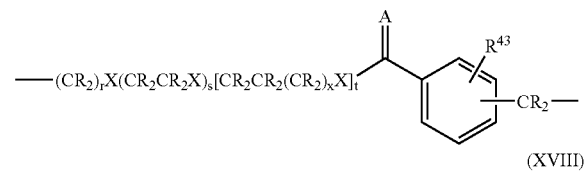

(XVII)

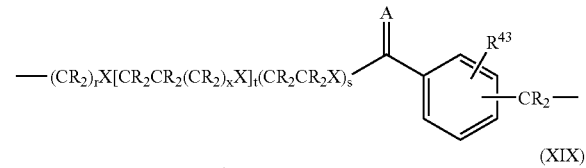

(XVIII)

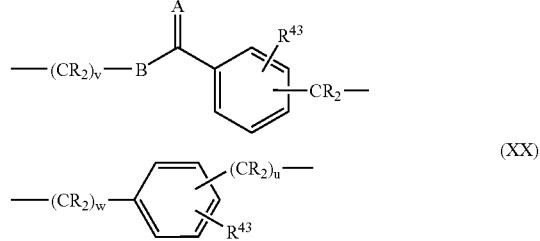

(XIX)

(XX)

where
r is in a range between about 1 and about 10, preferably 2 or 3;
s is in a range between about 0 and about 100, preferably 4 to 20;
t is in a range between about 0 and about 100, preferably in a range between about 0 and about 20, and most preferably 0;
u is in a range between about 1 and about 10, preferably 1;
v is in a range between about 1 and about 10, preferably 2 or 3;
w is 1 or 2;
x is 1 or 2;
X is O, NOH, NOR or NR, preferably O;
wherein R is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;
wherein $R^{43}$ is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen. $R^{43}$ is preferably H. If $R^{43}$ represents an aryl group, it can be fused to the ring in Formulas (XVII) through (XX);
A is O, NOH, NOR, NR or S, preferably O;
B is O, NOH, NOR, NR or S, preferably O or NR and most preferably O;
and where the polysiloxane or the silicone resin is bound to the $(CR_2)_r$ (Formula XIV, XV, XVII, and XVIII), $(CR_2)_v$ (Formula XVI and XIX), or $(CR_2)_w$ (Formula XX). Any of the linker structures shown in Formulas (XIV) through (XX)

can also be interrupted with cycloaliphatic rings or aromatic rings. Substituents on the phenyl group of formulas (XVII), (XVIII), (XIX), and (XX) may be present at any free valence site. The polysiloxane or silicone resin may or may not contain other functionalities by substitution at silicon atoms either the same as or distinct from those bound to the linking groups described above, such as amine-, polyether-, alkyl-, or heteroalkyl-containing groups.

The linker is typically derived from a polysiloxane or silicone resin bound linker precursor which comprises a linker bound to a leaving group (L). Illustrative leaving groups include halides such as chloride, bromide and iodide; tosylate, mesylate, phosphate; cyclic leaving groups (that is, those in which the leaving group remains bound in the linker) such as epoxy or other cyclic leaving group containing at least one heteroatom; and other leaving groups known to those skilled in the art. Preferred leaving groups are bromide, chloride, and iodide. In synthesis, a molecular hook replaces the leaving group so that the linker becomes bound to a molecular hook.

The method for making the silicone compositions of the present invention includes combining a molecular hook, a polysiloxane or silicone resin, and a linker. The sequence of addition can be varied, for example, the linker and the molecular hook can be combined and this combination can be sequentially combined with a polysiloxane or a silicone resin. Preferably, the linker is combined with a polysiloxane or silicone resin to form a linker-substituted polymer and the combination is sequentially combined with the molecular hook to form a hook-linker-polymer product. Preparation techniques for the silicone compositions of the present invention also include synthesizing a silicone composition with a halide counterion, and then exchanging the counterion with a hexafluorophosphate counterion, a tetrafluoroborate counterion, or a triflate counterion.

Typically, the silicone composition of the present invention incorporates the linker of formula (XX) by (1) allowing a hydride functional silicone material to react with an isomer or isomer mixture of vinylbenzyl halide in the presence of a hydrosilylation catalyst; and (2) allowing the benzyhalide-substituted polymer to react with a molecular hook. Typically, the vinylbenzyl halide is vinylbenzyl chloride.

Typically, the silicone composition of the present invention incorporates the linkers of formula (XVII), (XVIII), and (XIV) by (1) allowing a hydride functional silicone material to react with an allyl alcohol or an allyl-substituted polyether in the presence of a hydrosilylation catalyst; (2) esterifying the terminal carbinol groups with a halomethyl benzoyl halide of halomethylbenzoic acid; and (3) allowing the benylhalide-substituted polymer to react with a molecular hook.

Typically, the silicone composition of the present invention incorporates the linker of formula (XIV), (XV), and (XVI) by (1) allowing a hydride functional silicone material to react with an allyl alcohol or an allyl-substituted polyether in the presence of a hydrosilylation catalyst; (2) esterifying the terminal carbinol groups with a haloacetic acid or haloacetyl halide; and (3) allowing the haloacetate-substituted polymer to react with a molecular hook.

Silicone compositions of the present invention which include at least one polysiloxane or silicone resin, at least one linker, and at least one molecular hook typically impart cosmetic and other durable benefits in products such as hair care products, but also including textile care products, cosmetic products, oral care products, and animal care products. A particular advantage of the present invention is that many of the described functional groups provide solubility to the silicone composition in consumer relevant media as well as the potential for additional hair care benefits which may or may not be typically associated with the functional groups of the linker.

The silicone compositions can be delivered to a substrate, for example hair, in any appropriate formulation, for example water or water and alcohol mixtures which can contain in a range between about 1% by weight and about 99% by weight alcohol based on the total formulation.

In order that those skilled in the art will be better able to practice the invention, the following examples are given by way of illustration and not by way of limitation.

In the following examples, $D^{R1}$ and $D^{R2}$ are defined as follows:

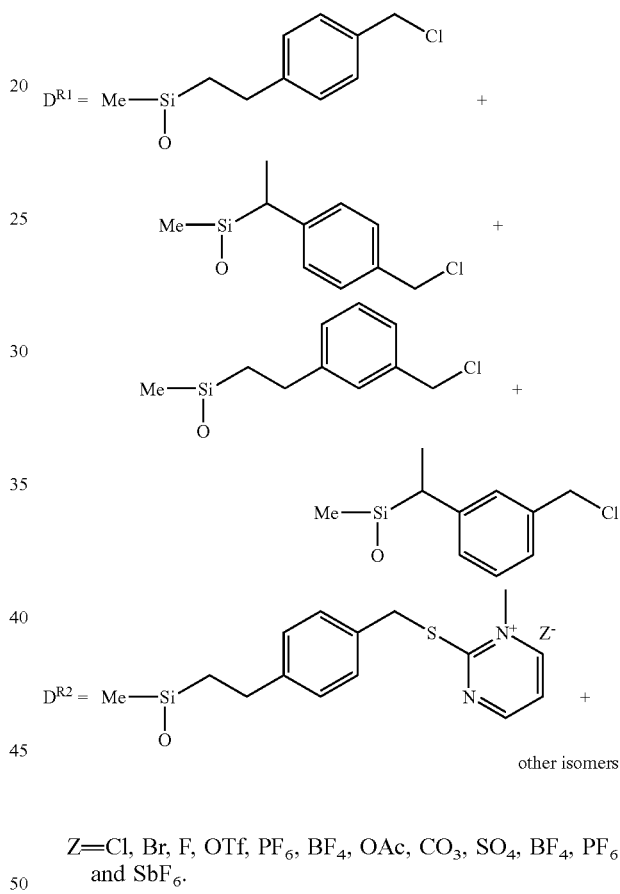

$Z$=Cl, Br, F, OTf, $PF_6$, $BF_4$, OAc, $CO_3$, $SO_4$, $BF_4$, $PF_6$ and $SbF_6$.

EXAMPLE 1

Silicone hydride fluid ($MD_{48}D^H{}_3M$). A 1000 mL three-neck round bottom flask equipped with a mechanical stirrer, thermometer attached to a temperature controlling device and a drying tube was charged with a silanol-terminated polydimethylsiloxane polymer (535.1 grams, 7.23 mol dimethylsiloxy groups), a silicone hydride fluid ($MD^H{}_xM$, 30.35 grams=0.48 mol methylhydridosiloxy groups +0.019 mol trimethylsiloxy groups), hexamethyldisiloxane (24.41 grams, 0.3 mol trimethylsiloxy groups) and a linear phosphonitrilo catalyst (2.95 grams of a 2% solution in silicone fluid, 100 ppm). The mixture was stirred at 90° C. for two hours after which it was cooled and treated with magnesium oxide (1 gram, 0.0256 mol). The mixture was filtered through Celite to furnish the product as a clear, colorless fluid. Viscosity=58.8 centistokes; hydride level=828 ppm. $^1$H NMR (acetone-$d_6$): δ4.74 (s, 3.0H, SiH), 0.12 (m, 315.0H, SiMe).

EXAMPLE 2

Benzylchloride-substituted silicone polymer ($M_{48}D^{R1}_3M$), A 5 L three-neck round bottom flask equipped with a stirbar, thermometer attached to a temperature controlling device, addition funnel and a condenser with a drying tube was charged with the silicone hydride polymer $MD_{48}D^H_3M$ (931.2 grams, 0.77 mol hydride), 4-vinylbenzyl chloride (7.56 g, 0.050 mol), di-t-butylphenol (0.52 g) and Karstedt's catalyst (95.3 mg of a 10% Pt solution). The mixture was heated to 60° C. and additional 4-vinylbenzyl chloride (110.16 g, 0.72 mol) was added over 60 minutes with a slight exotherm to 80° C. The reaction was followed by gasiometric hydride analysis and was finished within 6 hours after the addition was complete. The reaction mixture was distilled at 130° C. under vacuum to remove unreacted volatile compounds. Viscosity=124 centistokes. $^1$H NMR (acetone-$d_6$): δ7.33 (m, 6.0H, phenyl), 7.22 (m, 6.0H, phenyl), 4.66 (s, 6.0H, CH$_2$Cl), 2.73 (m, 6.0H, SiCH$_2$CH$_2$Ar), 2.24 (m, 3.0H, SiCH(CH$_3$)Ar), 1.39 (m, 9.0H, SiCH(CH$_3$)Ar), 0.93 (m, 6.0H, SiCH$_2$CH$_2$Ar), 0.12 (m, 315H, SiMe).

EXAMPLE 3

Pyrimidinium-substituted silicone ($MD_{49}D^{R2}_{3.4}M$), iodide counterion. To a 500 mL round bottom flask containing a stir bar was added 115.0 g (25.45 mmol) of the benzylchloride-substituted silicone $MD_{49}D^{R1}_{3.4}M$. Sodium iodide (12.71 g, 84.80 mmol) and 1-methylpyrimidine-2-thione (10.37 g, 82.17 mmol) were added piecewise as solids. The mixture was combined with acetonitrile and stirred using a mechanical stirrer for 44 hours at 55° C. After this time, the mixture was allowed to settle. The acetonitrile was decanted and the polymer washed twice with acetonitrile in the same manner. The polymer was concentrated with a rotary evaporator and then dissolved in acetone. The mixture was filtered, through a medium frit to remove salt. The acetone solutions were collected and dried under vacuum. The product was isolated in 79.7% yield (106.6 g) as a waxy, red-orange solid. $^1$H NMR (acetone-$d_6$): δ9.74 (br s, 3.4H, pyH), 9.36 (br s, 3.4H, pyH), 8.01 (br s, 3.4 H, pyH), 7.47–7.21 (m, 13.6H, phenyl), 4.80 (s, 6.8H, CH$_2$S), 4.33 (s, 10.2H, NMe), 2.69 (m, 453H, SiCH$_2$CH$_2$Ar), 2.22 (m, 1.13H, SiCH(Me)Ar), 1.38 (m, 3.39H, SiCH(Me)Ar), 0.90 (m, 4.53H, SiCH$_2$CH$_2$Ar), 0.12 (s, 316.2H, SiMe). Note that other solvents can be used in place of acetone in the final step, such as Isopar C.

EXAMPLE 4

Pyrimidinium-substituted silicone ($MD_{49}D^{R2}_{3.4}M$), tetrafluoroborate counterion. 25 g (5.33 mmol) of $MD_{49}D^{R1}_{3.4}M$, 2.47 g (22.5 mmol) of NaBF$_4$, 2.25 g (17.8 mmol) of 1-methyl-2-pyrimidinethione and 34 g of acetonitrile were added to a flask. The reaction mixture was heated to ca. 85° C. for 120 hours; the course of the reaction was monitored by $^1$H NMR spectroscopy. The reaction was allowed to cool and was then centrifuged to separate the precipitated material. The supernatant was collected and the solvent was removed by evaporation under reduced pressure to a thick syrup. To the syrup was added 120 mL of absolute ethanol. The clear solution was centrifuged again to separate more precipitated salt, and the mother liquors were decanted, collected and combined. The addition of 10 mL of water caused the polymer product to precipitate. The mixture was then centrifuged, and the polymer phase was collected. The volatile materials were removed by evaporation under reduced pressure for 16 hours at room temperature to yield 20 g of rubbery amber solid. $^1$H NMR (acetone-$d_6$)δ: 9.31 (s, 3.4H), 9.21 (s, 3.4H), 7.94 (s, 3.4H), 7.48–7.0 (m, 27.2H), 4.82 (s, 6.8H), 4.34 (s, 10.2H), 2.72 (m, 4.53H), 2.20 (q, J=7.4 Hz, 1.13H), 1.39, (m, 3.4H), 0.92 (m, 4.53H), 0.12 (s, 298.2H). Note that this reaction can be performed in higher boiling solvents, such as propionitrile, or in a sealed flask at higher temperatures, to speed the reaction.

EXAMPLE 5

Pyrimidinium-substituted silicone ($M^{R2}D_{48}M^{R2}$), tetrafluoroborate counterion. A flask was charged with 25 g (6.25 mmol) of $M^{R2}D_{48}M^{R2}$, 1.64 g (15.0 mmol) of NaBF$_4$, 1.49 g (11.8 mmol) of 1-methyl-2-pyrimidinethione and 34 g of acetonitrile. The reaction mixture was heated to ca. 85° C. for 168 hours, monitoring by $^1$H NMR, after which time it was allowed to cool. It was then centrifuged to separate the precipitated material. The supernatant was collected, and the solvent was removed by evaporation under reduced pressure to a thick syrup. To the syrup was added 120 mL of absolute ethanol. The clear solution was centrifuged again to remove the formed precipitate, and the mother liquors were decanted, collected and combined. The addition of 10 mL of water caused the polymer product to precipitate. The mixture was then centrifuged, and the polymer phase was collected. The volatile materials were removed by evaporation under reduced pressure for 16 hours at room temperature to yield 20 g of rubbery amber solid. $^1$H NMR (acetone-$d_6$)δ:9.36 (s, 2H), 9.31 (s, 2H), 7.99 (s, 2H), 7.48–7.0 (m, 8H), 4.82 (s, 4H), 4.34 (s, 6H), 2.72 (m, 2.66H), 2.20 (q, J=7.4 Hz, 0.66H), 1.39 (m, 2H), 0.92 (m, 2.66H), 0.12 (s, 312H).

EXAMPLE 6

Pyrimidinium-substituted silicone ($MD_{49}D^{R2}_{3.4}M$), hexafluorophosphate counterion. To a vessel was added $MD_{49}D^{R1}_{3.4}M$ (0.5 g, 0. 11 mmol), NaPF$_6$, (0.055 g, 0.33 mmol), 1-methyl-2-pyrimidinethione (0.045 g, 0.33 mmol) and acetonitrile (5 g). The reaction vessel was tightly sealed, and the reaction was heated to 115° C. for 72 hours. The reaction mixture was allowed to cool, and the solvent was removed by evaporation under reduced pressure. Analysis of the residue by $^1$H NMR indicated that the desired product had formed in 91% yield. $^1$H NMR (acetone-$d_6$)δ:9.51 (s, 3.4H), 9.36 (s, 3.4H), 8.00 (s, 3.4H), 7.48–7.0 (m, 27.2H) 4.82 (s, 6.8H), 4.34 (s, 10.2H), 2.72 (m, 4.53H), 2.20 (q, J=7.4Hz, 1.13H), 1.39 (m, 3.4H), 0.92 (m, 4.53H), 0.12 (s, 298.2H).

EXAMPLE 7

Pyrimidinium-substituted silicone ($MD_{49}D^{R2}_{3.4}M$), alternative counterions. The new, alternative counterion polymers can also be prepared by synthesizing the iodide polymer, and then exchanging the counterion with an alternative. The $MD_{49}D^{R2}_{3.4}M$ polymer containing the iodide counterion was dissolved in diethyl ether such that the solution contained 10% silicone by weight. A saturated aqueous solution of the salt of the desired counterion was also prepared. The ether solution containing the polymer was washed with an equal volume of the aqueous salt solution two times. The organic layer was dried over activated 4 Å molecular sieves. The volatile materials were removed under reduced pressure to yield the neat polymer with the exchanged counterion. NMR spectroscopy was used to confirm that exchange had occurred. Examples of salts used are sodium chloride, sodium bromide, sodium triflate, sodium carbonate, sodium sulfate, sodium hexafluorophosphate, sodium tetrafluoroborate, silver hexafluorophosphate, silver triflate, sodium fluoride, and potassium carbonate.

Silicone deposition. Polymers described in this invention impart durable benefits to hair such as good combability, manageability, etc with the advantage of greater thermal stability. The degree to which the new silicone materials interact with hair durably after multi-shampoo and reapplication cycles was measured. Hair switches (4 grams) were contacted with a 45/45/10 butyl lactate/vaerolactone/water solution containing 2% of a given polymer by weight for 5 min at either pH 7 or pH 9.5. Following treatment, the hair switches were rinsed, extracted overnight in the solvent mixture and shampooed with Prell® 24 times. The hair switches were analyzed by x-ray fluorescence (XRF) following treatment/extraction as well as after 24 shampoos. The counts were converted to ppm silicon deposition using standard methods. Control experiments under the same conditions only without added polymer show no silicon deposition by XRF. The data from samples treated at pH 7 are shown in Table 1 and from those treated at pH 9.5 in Table 2.

TABLE 1

| Polymer | Initial Silicone Deposition (ppm)[1] | Silicone Remaining after 24 shampoos (ppm)[1] |
|---|---|---|
| $MD_{49}D^{R2}_{3.4}M$, iodide counterion | 2683 | 560 |
| $MD_{49}D^{R2}_{3.4}M$, $BF_4$ counterion | 3999 | 499 |

[1]Reported values are the average of measurements taken on three different hair switches treated under the same conditions.

TABLE 2

| Polymer | Initial Silicone Deposition (ppm)[1] | Silicone Remaining after 24 shampoos (ppm)[1] |
|---|---|---|
| $MD_{49}D^{R2}_{3.4}M$, iodide counterion | 3941 | 485 |
| $MD_{49}D^{R2}_{3.4}M$, $BF_4$ counterion | 4932 | 436 |

[1]Reported values are the average of measurements taken on three different hair switches treated under the same conditions.

The data in Tables 1 and 2 clearly show that this class of polymer is very durable on hair, with significant silicone levels remaining on the hair even after 24 shampoos with Prell®.

Thermal stability. The relative thermal stability of the new polymers was evaluated. Samples of the benzyl-substituted polymers containing chloride, iodide, hexafluorophosphate, tetrafluoroborate and triflate counterions were dissolved, in separate experiments, in acetone and isooctane, and monitored by $^1H$ NMR spectroscopy over 4 weeks at 40° C. in acetone or in isooctane. Results of the % decomposition can be seen in Tables 3 (acetone) and 4 (isooctane).

TABLE 3

| Counterion | % Decomposition |
|---|---|
| Chloride ($Cl^-$) | 90 |
| Iodide ($I^-$) | 60 |
| Hexafluorophosphate ($PF_6^-$) | 25 |
| Tetrafluoroborate ($BF_4^-$) | 15 |
| Triflate ($OTf^-$) | 15 |

TABLE 4

| Counterion | % Decomposition |
|---|---|
| Chloride ($Cl^-$) | 10 |
| Iodide ($I^-$) | 6 |
| Hexafluorophosphate ($PF_6^-$) | 2 |
| Tetrafluoroborate ($BF_4^-$) | 2 |
| Triflate ($OTf^-$) | 2 |

Tables 3 and 4 clearly show that the polymers containing the $PF_6^-$, $BF_4^-$ and OTf counterions were surprisingly more stable than the polymers with iodide or chloride counterions. This is a clear advantage of these polymer systems.

Wet combing. The polymers described in the present invention also exhibit wet combing benefits that are durable over repeated shampoo cycles. Hair switches (4 grams) were contacted with a 45/45/10 butyl lactate/valerolactone/water mixture containing 1% of a given polymer by weight for 4 minutes at pH 9.5. Combing force was measured using a standard Instron combing apparatus as a function of Prell® shampoo cycles. The results are shown in Table 5.

TABLE 5

| | Wet combing force[1] | | |
|---|---|---|---|
| Treatment | Initial | After 2 shampoos | After 24 shampoos |
| Untreated hair | 584 | 396 | 2000 |
| $MD_{49}D^{R2}_{3.4}M$, iodide counterion | 165 | 153 | 269 |
| $MD_{49}D^{R2}_{3.4}M$, $BF_4$ counterion | 132 | 131 | 445 |

The results shown in Table 5 clearly show that treatment of hair with the polymers described in the present invention can provide durable combing benefits.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A silicone composition which comprises at least one polysiloxane or silicone resin, at least one linker, and at least one molecular hook wherein the molecular hook comprises a hexafluorophosphate counterion, a tetrafluoroborate counterion, or combinations thereof.

2. The composition in accordance with claim 1, wherein the at least one linker is bound to a polysiloxane or silicone resin through a silicon, carbon, oxygen, nitrogen, or sulfur atom.

3. The composition in accordance with claim 2, wherein the at least one linker is bound to a polysiloxane or silicone resin through a silicon atom.

4. The composition in accordance with claim 1, having the formula $$M_a M'_b D_c D'_d T_e T'_f Q_g$$

where the subscripts a, b, c, d, e, f and g are zero or a positive integer, subject to the limitation that the sum of the subscripts b, d and f is at least one; where M has the formula:

$$R^{37}_3 SiO_{1/2},$$

M' has the formula:

$$(Z-Y)_h R^{38}_{3-h} SiO_{1/2},$$

D has the formula:

$$R^{39}_2 SiO_{2/2},$$

D' has the formula:

$$(Z-Y)_{(2-i)} R^{40}_i SiO_{2/2},$$

T has the formula:

$$R^{41} SiO_{3/2},$$

T' has the formula:

$$(Z-Y) SiO_{3/2},$$

and Q has the formula $SiO_{4/2}$, where subscript h is in a range between 1 and 3; subscript i is 0 or 1; each $R^{37}$, $R^{38}$, $R^{39}$, $R^{40}$, $R^{41}$ is independently at each occurrence a hydrogen atom, $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, polyether, or amino alkyl; each Z, independently at each occurrence, is a molecular hook; and each Y, independently at each occurrence, is a linker.

5. The composition of claim 4, comprising at least one compound of the following formulas, (VII), (VIII), (IX), (X), (XI), (XII), or (XIII):

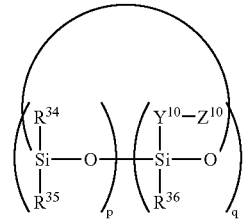
(VII)

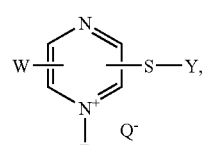 
(VIII)

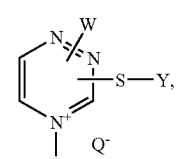
(IX)

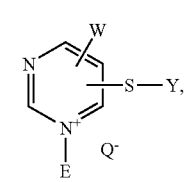
(X)

(XI)

(XII)

$$M_a M'_b Q_g$$ (XIII)

where each $R^{1-36}$ is independently at each occurrence a hydrogen atom, $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, polyether, or amino alkyl; $Z^{1-10}$, is independently at each occurrence a molecular hook; and $Y^{1-10}$, independently at each occurrence, is a linker; wherein "m" in each formula has a value in a range between about 0 and about 13,000; "n" in each formula has a value in a range between about 0 and about 13,000 with the proviso that in formula (VIII) "n" is not 0; "m+n" in each formula has a value in a range between about 1 and about 26,000; "q" has a value of at least one "p+q" has a value of at least 3; "a", "b", and "g" have a value of at least one.

6. The composition in accordance with claim 5, comprising at least one compound of formulas (VII), (VIII), (X), or (XI) wherein $R^{1-33}$ is methyl; "m" in each formula has a value in a range between about 15 and about 120; and "m+n" in each formula has a value in a range between about 15 and about 120.

7. The composition in accordance with claim 5, comprising at least one compound of formula (XII), wherein "p+q" has a value in a range between about 3 and about 6; and $R^{34-36}$ is methyl.

8. The composition in accordance with claim 1, wherein the molecular hook comprises a heterocyclic pyridinium compound (VII), a heterocyclic triazinium (VIII), a heterocyclic pyrimidinium compound (IX), or a heterocyclic pyrazine compound (X):

-continued

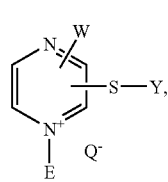
(X)

wherein Y is a linker; W is hydrogen or is selected from electron withdrawing, electron neutral, or electron donating groups with Hammett sigma para values between −1.0 and +1.5 comprising carbon-linked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1(NE^2)$, $SONE^1E^2$; O-linked groups including $OE^1$, OCN, $ONE^1E^2$; N-linked groups including $NE^1E^2$, $NE^1E^2E^{3+}$, $NE^1OE^2$, $NE^1SE^2$, NCO, NCS, $NO_2$, $N=NE^1$, $N=NOE^1$, $NE^1CN$, $N=C=NE^1$, $NE^1NE^2E^3$, $NE^1NA^2NA^3A^4$, $NA^1N=NE^2$; other groups including $CONE^1_2$, $CONE^1COE^2$, $C(=NE^1)NE^1E^2$, CHO, CHS, CN, NC, Hal, and derived groups that connect one or more of the optional substituents via a ring system; Hal is fluorine, chlorine, bromine, or iodine; and wherein E, $E^1$, $E^2$, $E^3$, and $E^4$ each represent, independently from one another, a monovalent group which can be silicone group, H, or any of the following: a straight, branched or mono- or polycyclic aliphatic, mono- or polyunsaturated alkyl, aryl, heteroalkyl, heteroaliphatic or heteroolefinic system including carbon atoms in a range between about 1 and about 30 together with heteroatoms in a range between about 0 and about 15, including oxygen, nitrogen, sulfur, phosphorus, silicon and incorporating one or more substituents including mono, poly or perfluoro substitution; and wherein $Q^-$ is the counterion.

9. The composition in accordance with claim 1, wherein the molecular hook comprises a compound of the formula (V) or formula (VI):

(V)

(VI)

wherein R is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;

Q is the counterion;

L is the linker; and j is in a range between about 1 and about 15.

10. The composition in accordance with claim 1, wherein the linker comprises a $C_1$–$C_{250}$ alkyl, aryl, or alkylaryl group optionally containing one or more heteroatoms.

11. The composition in accordance with claim 10, wherein the linker comprises at least one compound of the formula (XIV), (XV), (XVI), (XVII), (XVIII), (XIX), or (XX):

(XIV)
—$(CR_2)_rX(CR_2CR_2X)_s[CR_2CR_2(CR_2)_wX]_t$—$(CR_2)_u$—

(XV)
—$(CR_2)_rX[CR_2CR_2(CR_2)_wX]_t(CR_2CR_2X)_s$—$(CR_2)_u$—

(XVI)
—$(CR_2)_v$—B—$(CR_2)_u$—

(XVII)
—$(CR_2)_rX(CR_2CR_2X)_s[CR_2CR_2(CR_2)_xX]_t$—$R^{43}$
—$CR_2$—

(XVIII)
$(CR_2)_rX[CR_2CR_2(CR_2)_xX]_t(CR_2CR_2X)_s$—$R^{43}$
—$CR_2$—

(XIX)
—$(CR_2)_v$—B—$R^{43}$
—$CR_2$—

(XX)
—$(CR_2)_w$—$(CR_2)_u$—
$R^{39}$ where
r is in a range between about 1 and about 10;
s is in a range between about 0 and about 100;
t is in a range between about 0 and about 100;
u is in a range between about 1 and about 10;
v is in a range between about 1 and about 10;
w is 1 or 2;
x is 1 or 2;
X is O, NOH, NOR, or NR;
wherein R is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;
wherein $R^{43}$ is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen;

A is O, NOH, NOR, NR or S;
B is O, NOH, NOR, NR or S; and
where the polysiloxane or the silicone resin is bound to the (CR$_2$)$_r$ (Formula XIV, XV, XVII, and XVIII), (CR$_2$)$_v$ (Formula XVI and XIX), or (CR$_2$)$_w$ (Formula XX).

12. The composition in accordance with claim 11, wherein r is 2 or 3; s is in a range between about 4 and about 20; t is 0; u is 1; v is 2 or 3; w is 1 or 2; x is 1 or 2; X is O; R is H; R$^{43}$ is H; A is O; and B is O.

13. The composition in accordance with claim 1, wherein the silicone composition has a percent decomposition of less than about 30% for a time period of 4 weeks at a temperature of about 40° C. in acetone.

14. A hair care product comprising the composition of claim 1.

15. A method for providing adhesion of polysiloxane or silicone resin to hair which comprises treating hair with the composition of claim 1.

16. A silicone composition comprising at least one compound of the formula (VIII):

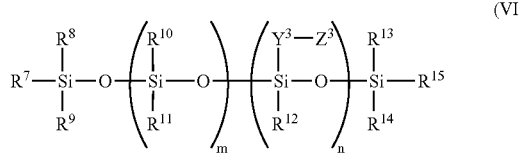
(VIII)

where each R$^{7-15}$ is methyl; Z$^3$ is a pyrimidinium molecular hook of the formula (III)

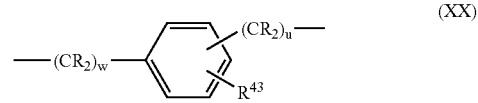
(III)

wherein W is hydrogen, E is methyl; Q$^-$ is hexafluorophosphate, tetrafluoroborate, or combinations thereof; and Y is a linker of the formula (XX):

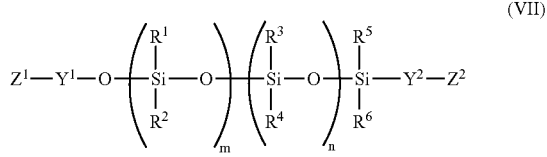
(XX)

wherein u is 1; w is 1 or 2; R is H; R$^{43}$ is H; and where the polysiloxane is bound to the (CR$_2$)$_w$ (Formula XX).

17. A silicone composition comprising at least one compound of the formula (VII):

(VII)

where each R$^{1-6}$ is methyl; Z$^{1-2}$ are each a pyrimidinium molecular hook of the formula (III):

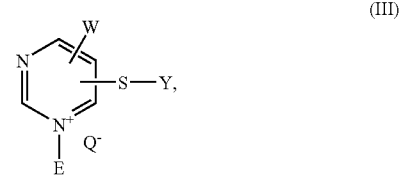
(III)

wherein W is hydrogen, E is methyl; Q$^-$ is hexafluorophosphate, tetrafluoroborate, or combinations thereof; and Y is a linker of the formula (XX):

(XX)

wherein u is 1; w is 1 or 2; R is H; R$^{43}$ is H; and where the polysiloxane is bound to the (CR$_2$)$_w$ (Formula XX).

18. A method for making a silicone composition comprising
(1) reacting at least one polysiloxane or silicone resin with at least one linker to form a linker-substituted polymer; and
(2) reacting the linker-substituted polymer with at least one molecular hook to form a hook-linker-polymer product wherein the molecular hook moiety in the product comprises a hexafluorophosphate counterion, a tetrafluoroborate counterion, or combinations thereof.

19. The method in accordance with claim 18, wherein the at least one linker is bound to a polysiloxane or silicone resin through a silicon, carbon, oxygen, nitrogen, or sulfur atom.

20. The method in accordance with claim 19, wherein the at least one linker is bound to a polysiloxane or silicone resin through a silicon atom.

21. The method in accordance with claim 18, wherein the silicone composition has the formula M$_a$M'$_b$D$_c$D'$_d$T$_e$T'$_f$Q$_g$ where the subscripts a, b, c, d, e, f and g are zero or a positive integer, subject to the limitation that the sum of the subscripts b, d and f is at least one; where M has the formula:

R$^{37}$$_3$SiO$_{1/2}$,

M' has the formula:

(Z-Y)$_h$R$^{38}$$_{3-h}$SiO$_{1/2}$,

D has the formula:

R$^{39}$$_2$SiO$_{2/2}$,

D' has the formula:

(Z-Y)$_{(2-i)}$R$^{40}$$_i$SiO$_{2/2}$,

T has the formula:

R$^{41}$SiO$_{3/2}$,

T' has the formula:

(Z-Y)SiO$_{3/2}$, and Q has the formula SiO$_{4/2}$, where subscript h is in a range between 1 and 3; subscript i is 0 or 1; each R$^{37}$, R$^{38}$, R$^{39}$, R$^{40}$, R$^{41}$ is independently at each occurrence a hydrogen atom, $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, polyether, or amino alkyl; each Z, independently at each occurrence, is a molecular hook; and each Y, independently at each occurrence, is a linker.

22. The method in accordance with claim 21, wherein the silicone composition comprises at least one compound of the following formulas, (VII), (VIII), (IX), (X), (XI), (XII), or (XIII):

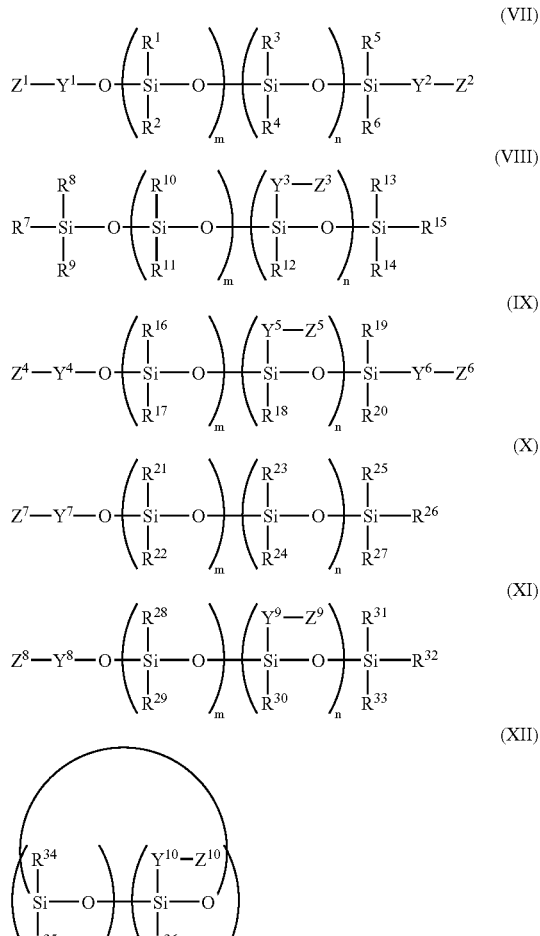

$$M_a M'_b Q_g \quad (XIII)$$

where each $R^{1-36}$ is independently at each occurrence a hydrogen atom, $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, polyether, or amino alkyl; $Z^{1-10}$, is independently at each occurrence, is a molecular hook; and $Y^{1-10}$, independently at each occurrence, is a linker; wherein "m" in each formula has a value in a range between about 0 and about 13,000; "n" in each formula has a value in a range between about 0 and about 13,000 with the proviso that in formula (VIII) "n" is not 0; "m+n" in each formula has a value in a range between about 1 and about 26,000; "q" has a value of at least one "p+q" has a value of at least 3; "a","b", and "g" have a value of at least one.

23. The method in accordance with claim 22, wherein the silicone composition comprises at least one compound of the formula (VII), (VIII), (X), or (XI) wherein $R^{1-33}$ is methyl; "m" in each formula has a value in a range between about 15 and about 120; and "m+n" in each formula has a value in a range between about 15 and about 120.

24. The method in accordance with claim 22, wherein the silicone composition comprises at least one compound of formula (XII) wherein "p+q" has a value in a range between about 3 and about 6; and $R^{34-36}$ is methyl.

25. The method in accordance with claim 18, wherein the molecular hook comprises a heterocyclic pyridinium compound, a heterocyclic triazinium compound, a heterocyclic pyrimidinium compound, or a heterocyclic pyrazine compound.

26. The method in accordance with claim 25, wherein the molecular hook is at least one member selected from the group consisting of a heterocyclic pyridinium compound (I), a heterocyclic triazinium compound (II), a heterocyclic pyrimidinium compound (III), and a heterocyclic pyrazine compound (IV):

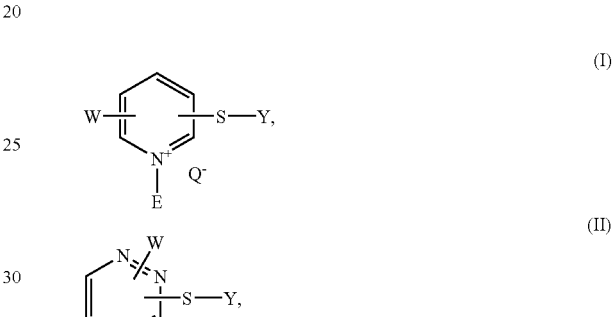

wherein Y is the linker; w is hydrogen or is selected from electron withdrawing, electron neutral, or electron donating groups with Hammett sigma para values between −1.0 and +1.5 comprising carbon-linked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1(NE^2)$, $SONE^1E^2$; O-linked groups including $OE^1$, OCN, $ONE^1E^2$; N-linked groups including $NE^1E^2$, $NE^1E^2E^{3+}$, $NE^1OE^2$, $NE^1SE^2$, NCO, NCS, $NO_2$, $N=NA^1$, $N=NOE^1$, $NE^1CN$, $N=C=NE^1$, $NE^1NE^2E^3$, $NE^1NE^2NE^3E^4$, $NE^1N=NE^2$; other groups including $CONE^1_2$, $CONE^1COE^2$, $C(=NE^1)NE^1E^2$, CHO, CHS, CN, NC, Hal, and derived groups that connect one or more of the optional substituents via a ring system; Hal is fluorine, chlorine, bromine, or iodine; and wherein E, $E^1$, $E^2$, $E^3$, and $E^4$ each represent, independently from one another, a monovalent group which can be the group, R, or H or any of the following: a straight, branched or mono- or polycyclic aliphatic, mono- or polyunsaturated alkyl, aryl, heteroalkyl, heteroaliphatic or heteroolefinic system including carbon atoms in a range between about 1 and about 30 together with heteroatoms in a range between about 0 and about 15, including oxygen, nitrogen, sulfur, phosphorus, silicon and incorporating one or more substituents including mono, poly or perfluoro substitution; and wherein the counterion, $Q^-$, is selected from the group consisting of hexafluorophosphate counterion, tetrafluoroborate counterion, and combinations thereof.

27. The method in accordance with claim 18, wherein the molecular hook comprises a compound of the formula (V) or formula (VI):

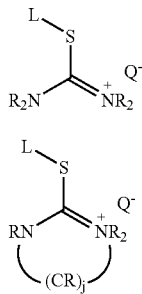

(V)

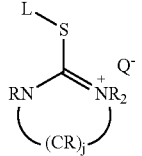

(VI)

wherein R is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;

$Q^-$ is the counterion;

L is the linker; and j is in a range between about 1 and about 15.

28. The method in accordance with claim 18, wherein the linker comprises a $C_1$–$C_{250}$ alkyl, aryl, or alkylaryl group optionally containing one or more heteroatoms.

29. The method in accordance with claim 28, wherein the linker comprises at least one compound of the formula (XIV), (XV), (XVI), (XVII), (XVIII), (XIX), or (XX):

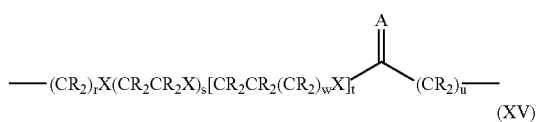

(XIV)

(XV)

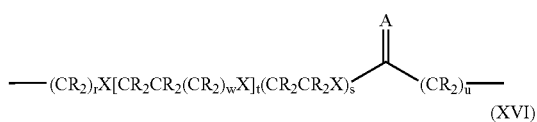

(XVI)

(XVII)

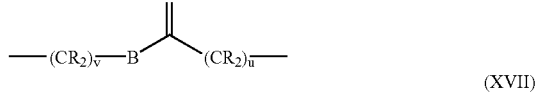

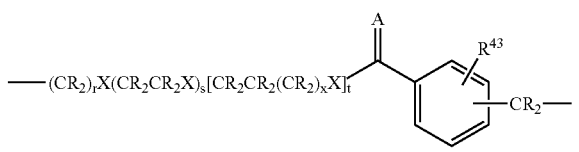

(XVIII)

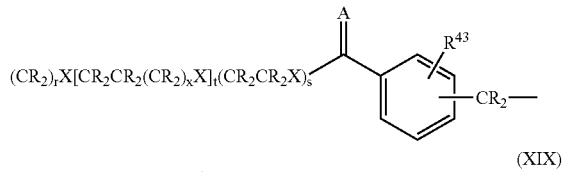

(XIX)

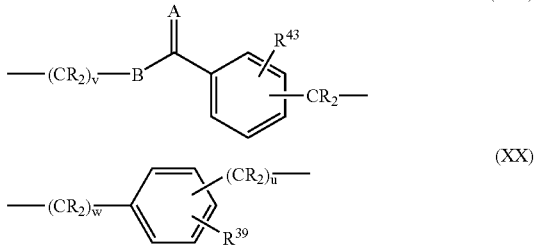

(XX)

where r is in a range between about 1 and about 10;

s is in a range between about 0 and about 100;

t is in a range between about 0 and about 100;

u is in a range between about 1 and about 10;

v is in a range between about 1 and about 10;

w is 1 or 2;

x is 1 or 2;

X is O, NOH, NOR or NR;

wherein R is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;

wherein $R^{43}$ is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen;

A is O, NOH, NOR, NR or S;

B is O, NOH, NOR, NR or S; and where the polysiloxane or the silicone resin is bound to the $(CR_2)_r$ (Formula XIV, XV, XVII, and XVIII), $(CR_2)_v$ (Formula XVI and XIX), or $(CR_2)_w$ (Formula XX).

30. The method in accordance with claim 29, wherein r is 2 or 3; s is in a range between about 4 and about 20; t is 0; u is 1; v is 2 or 3; w is 1 or 2; x is 1 or 2; X is O; R is H; $R^{43}$ is H; A is O; and B is O.

31. The method in accordance with claim 18, wherein the silicone composition has a percent decomposition of less than about 30% for a time period of 4 weeks at a temperature of about 40° C. in acetone.

32. A method for making a silicone composition comprising (1) reacting at least one polysiloxane and at least one benzyl-halide linker to form a benzyl-halide substituted polymer; and (2) reacting the benzyl-halide substituted polymer with at least one pyrimidinium molecular hook wherein the silicone composition comprises a polysiloxane compound of the formula (VIII):

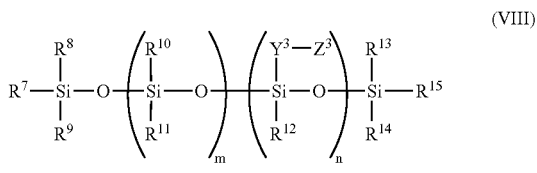
(VIII)

where each $R^{7-15}$ is methyl; Y is a linker of the formula (XX):

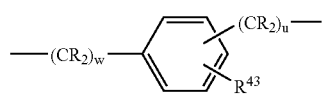
(XX)

wherein the polysiloxane is bound to the $(CR_2)_w$ (Formula XX); u is 1; w is 1 or 2; R is H; $R^{43}$ H; and $Z^3$ is the molecular hook of the formula (III)

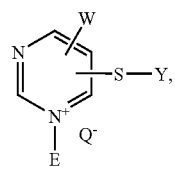
(III)

wherein W is hydrogen, E is methyl; and Q is a hexafluorophosphate counterion, a tetrafluoroborate counterion, or combinations thereof.

33. A method for making a silicone composition comprising (1) reacting at least one polysiloxane and at least one benzyl-halide linker to form a benzyl-halide substituted polymer; and (2) reacting the benzyl-halide substituted polymer with at least one pyrimidinium molecular hook wherein the silicone composition comprises a polysiloxane compound of the formula (VII):

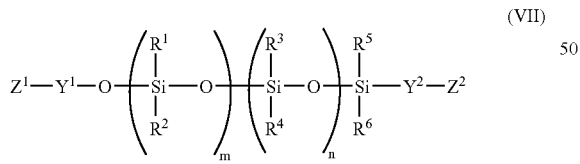
(VII)

where each $R^{1-6}$ is methyl; Y is a linker of the formula (XX):

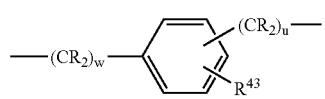
(XX)

wherein the polysiloxane is bound to the $(CR_2)_w$ (Formula XX); u is 1; w is 1 or 2; R is H; $R^{43}$ H; and $Z^{1-2}$ are each a pyrimidinium molecular hook of the formula (III):

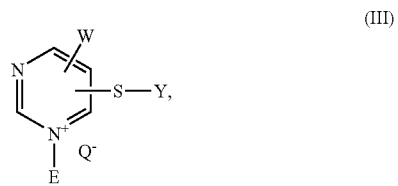
(III)

wherein W is hydrogen, E is methyl; and Q is a hexafluorophosphate counterion, a tetrafluoroborate counterion, or combination thereof.

34. A method for substantially increasing the thermal stability of a silicone composition comprising providing at least one molecular hook with a hexafluorophosphate counterion, a tetrafluoroborate counterion, or combinations thereof; a linker; and a polysiloxane or silicone resin wherein the silicone composition has a percent decomposition of less than about 30% for a time period of 4 weeks at a temperature of about 40° C. in acetone.

35. The method in accordance with claim 34, wherein the at least one linker is bound to a polysiloxane or silicone resin through a silicon, carbon, oxygen, nitrogen, or sulfur atom.

36. The method in accordance with claim 35, wherein the at least one linker is bound to a polysiloxane or silicone resin through a silicon atom.

37. The method in accordance with claim 34, wherein the silicone composition has the formula $$M_a M'_b D_c D'_d T_e T'_f Q_g$$

where the subscripts a, b, c, d, e, f and g are zero or a positive integer, subject to the limitation that the sum of the subscripts b, d and f is at least one; where M has the formula:

M' has the formula:

D has the formula:

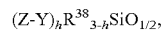

D' has the formula:

T has the formula:

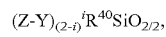

T' has the formula:

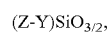

and Q has the formula $SiO_{4/2}$, where subscript h is in a range between 1 and 3; subscript i is 0 or 1; each $R^{37}$, $R^{38}$, $R^{39}$, $R^{40}$, $R^{41}$ is independently at each occurrence a hydrogen atom, $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, polyether, or amino alkyl; each Z, independently at each occurrence, is a molecular hook; and each Y, independently at each occurrence, is a linker.

38. The method in accordance with claim 37 in which the silicone composition comprises at least one compound of the following formulas, (VII), (VIII), (IX), (X), (XI), (XII), or (XIII):

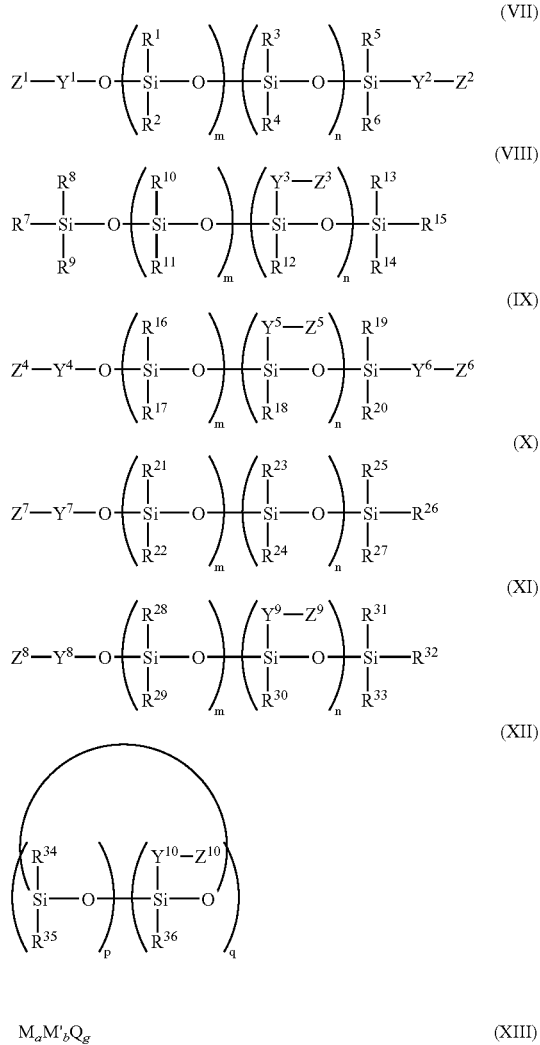

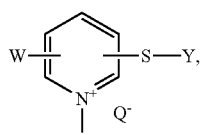

(I)

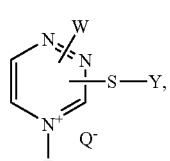

(II)

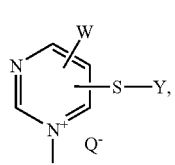

(III)

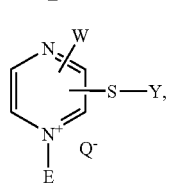

(IV)

where each $R^{1-36}$ is independently at each occurrence a hydrogen atom, $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, polyether, or amino alkyl; $Z^{1-10}$, is independently at each occurrence, is a molecular hook; and $Y^{1-10}$, independently at each occurrence, is a linker; wherein "m" in each formula has a value in a range between about 0 and about 13,000; "n" in each formula has a value in a range between about 0 and about 13,000 with the proviso that in formula (II) "n" is not 0; "m+n" in each formula has a value in a range between about 1 and about 26,000; "q" has a value of at least one "p+q" has a value of at least 3; "a","b", and "g" have a value of at least one.

39. The method in accordance with claim 38, wherein the silicone composition comprises at least one compound of formulas (VII), (VIII), (X), or (XI) wherein $R^{1-33}$ is methyl; "m" in each formula has a value in a range between about 15 and about 120; and "m+n" in each formula has a value in a range between about 15 and about 120.

40. The method in accordance with claim 38, wherein the silicone composition comprises at least one compound of formula (XII), wherein "p+q" has a value in a range between about 3 and about 6; and $R^{34-36}$ is methyl.

41. The method in accordance with claim 38, wherein the moiety Z-Y is prepared by a process which comprises combining a hook with a linker precursor comprising a linker and a leaving group.

42. The method in accordance with claim 41, wherein the leaving group is selected from the group consisting of chloride, bromide, iodide, tosylate, mesylate, phosphate, and cyclic leaving groups containing at least one heteroatom.

43. The method in accordance with claim 42, wherein the leaving group is iodide, chloride, or bromide.

44. The method in accordance with claim 34, wherein the molecular hook comprises a heterocyclic pyridinium compound (VII), a heterocyclic triazinium (VIII), a heterocyclic pyrimidinium compound (IX), or a heterocyclic pyrazine compound (X):

wherein Y is a linker; W is hydrogen or is selected from electron withdrawing, electron neutral, or electron donating groups with Hammett sigma para values between −1.0 and +1.5 comprising carbon-linked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1(NE^2)$, $SONE^1E^2$; O-linked groups including $OE^1$, OCN, $ONE^1E^2$; N-linked groups including $NE^1E^2$, $NE^1E^2E^{3+}$, $NE^1OE^2$, $NE^1SE^2$, NCO, NCS, $NO_2$, $N=NE^1$, $N=NOE^1$, $NE^1CN$, $N=C=NE^1$, $NE^1NE^2E^3$, $NE^1NA^2NA^3A^4$, $NA^1N=NE^2$; other groups including $CONE^1{}_2$, $CONE^1COE^2$, $C(=NE^1)NE^1E^2$, CHO, CHS, CN, NC, Hal, and derived groups that connect one or more of the optional substituents via a ring system; Hal is fluorine, chlorine, bromine, or iodine; and wherein E, $E^1$, $E^2$, $E^3$, and $E^4$ each represent, independently from one another, a monovalent group which can be silicone group, H, or any of the following: a straight, branched or mono- or polycyclic aliphatic, mono- or polyunsaturated alkyl, aryl, heteroalkyl, heteroaliphatic or heteroolefinic system including carbon atoms in a range between about 1 and about 30 together with heteroatoms in a range between about 0 and about 15, including oxygen, nitrogen, sulfur, phosphorus, silicon and incorporating one or more substituents including mono, poly or perfluoro substitution; and wherein Q⁻ is the counterion.

45. The method in accordance with claim 34, wherein the molecular hook comprises a compound of the formula (V) or formula (VI):

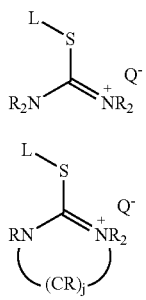

(V)

(VI)

wherein R is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;

Q is the counterion;

L is the linker; and j is in a range between about 1 and about 15.

46. The method in accordance with claim 34, wherein the linker comprises a $C_1$–$C_{250}$ alkyl, aryl, or alkylaryl group optionally containing one or more heteroatoms.

47. The method in accordance with claim 46, wherein the linker comprises at least one compound of the formula (XIV), (XV), (XVI), (XVII), (XVIII), (XIX), or (XX):

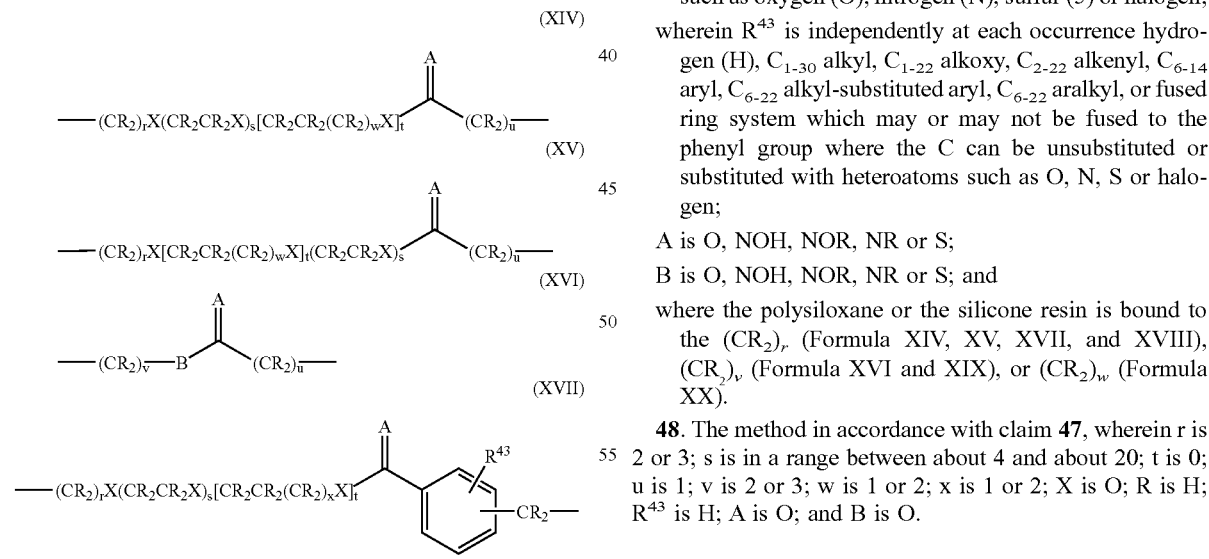

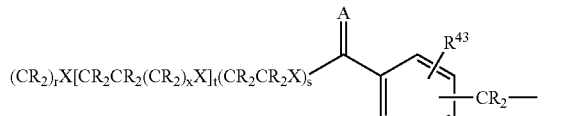

(XVIII)

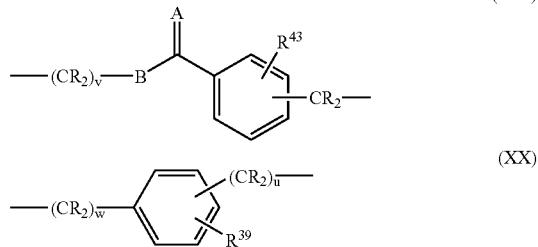

(XIX)

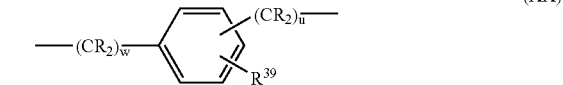

(XX)

where r is in a range between about 1 and about 10;

s is in a range between about 0 and about 100;

t is in a range between about 0 and about 100;

u is in a range between about 1 and about 10;

v is in a range between about 1 and about 10;

w is 1 or 2;

x is 1 or 2;

X is O, NOH, NOR, or NR;

wherein R is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (5) or halogen;

wherein $R^{43}$ is independently at each occurrence hydrogen (H), $C_{1-30}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen;

A is O, NOH, NOR, NR or S;

B is O, NOH, NOR, NR or S; and where the polysiloxane or the silicone resin is bound to the $(CR_2)_r$ (Formula XIV, XV, XVII, and XVIII), $(CR_2)_v$ (Formula XVI and XIX), or $(CR_2)_w$ (Formula XX).

48. The method in accordance with claim 47, wherein r is 2 or 3; s is in a range between about 4 and about 20; t is 0; u is 1; v is 2 or 3; w is 1 or 2; x is 1 or 2; X is O; R is H; $R^{43}$ is H; A is O; and B is O.

* * * * *